(12) United States Patent
Henke

(10) Patent No.: US 8,579,794 B2
(45) Date of Patent: Nov. 12, 2013

(54) AGITATOR TO STIMULATE THE CENTRAL NERVOUS SYSTEM

(75) Inventor: Reinhold Henke, Plymouth, MN (US)

(73) Assignee: Dymedix Corporation, Shoreview, MN (US)

( * ) Notice: Subject to any disclaimer, the term of this patent is extended or adjusted under 35 U.S.C. 154(b) by 209 days.

(21) Appl. No.: 12/434,042

(22) Filed: May 1, 2009

(65) Prior Publication Data

US 2009/0287265 A1    Nov. 19, 2009

Related U.S. Application Data

(60) Provisional application No. 61/049,802, filed on May 2, 2008.

(51) Int. Cl.
*A61M 21/00*    (2006.01)

(52) U.S. Cl.
USPC .......................................................... 600/27

(58) Field of Classification Search
USPC .......................................................... 607/3
See application file for complete search history.

(56) References Cited

U.S. PATENT DOCUMENTS

| | | |
|---|---|---|
| 3,478,344 A | 11/1969 | Schwitzgebel et al. |
| 3,483,861 A | 12/1969 | Tiep |
| 3,530,494 A | 9/1970 | Baratta |
| 3,572,316 A | 3/1971 | Vogelman et al. |
| 3,593,703 A | 7/1971 | Gunn et al. |
| 3,696,377 A | 10/1972 | Wall |
| 3,782,368 A | 1/1974 | Reibold |
| 3,802,417 A | 4/1974 | Lang |
| 3,827,301 A | 8/1974 | Parker |
| 3,998,209 A | 12/1976 | Macvaugh |
| 4,072,145 A | 2/1978 | Silva |
| 4,169,462 A | 10/1979 | Strube |
| 4,185,621 A | 1/1980 | Morrow |
| 4,220,142 A | 9/1980 | Rosen et al. |
| 4,267,845 A | 5/1981 | Robertson, Jr. et al. |
| 4,304,227 A | 12/1981 | Samelson |
| 4,308,872 A | 1/1982 | Watson et al. |
| 4,373,534 A | 2/1983 | Watson |
| 4,378,808 A | 4/1983 | Lichtenstein |
| 4,440,160 A | 4/1984 | Fischell et al. |

(Continued)

FOREIGN PATENT DOCUMENTS

| | | |
|---|---|---|
| EP | 0014693 B1 | 6/1983 |
| EP | 0171321 A1 | 2/1986 |

(Continued)

OTHER PUBLICATIONS

"Application Serial No. 09739237.7 Amended Claims Respnse filed Mar. 31, 2011", 12 pgs.

(Continued)

*Primary Examiner* — Christopher D Koharski
*Assistant Examiner* — Philip Edwards
(74) *Attorney, Agent, or Firm* — Schwegman Lundberg & Woessner, P.A.

(57) ABSTRACT

A tactile and audible sensation can be provided to a patient using a coiled or scrolled film in response to a received control signal. The tactile and audible sensation can be configured to stimulate the patient's central nervous system to sufficiently interrupt and undesirable sleep behavior of the patient, but avoid significantly changing a sleep state of the patient.

11 Claims, 4 Drawing Sheets

(56) References Cited

U.S. PATENT DOCUMENTS

| | | | |
|---|---|---|---|
| 4,443,730 A | 4/1984 | Kitamura et al. | |
| 4,452,252 A | 6/1984 | Sackner | |
| 4,456,015 A | 6/1984 | Sackner | |
| 4,499,394 A | 2/1985 | Koal | |
| 4,503,862 A | 3/1985 | Baessler | |
| 4,509,527 A | 4/1985 | Fraden | |
| 4,576,179 A | 3/1986 | Manus et al. | |
| 4,577,510 A | 3/1986 | Bur et al. | |
| 4,593,686 A | 6/1986 | Lloyd et al. | |
| 4,600,855 A | 7/1986 | Strachan | |
| 4,644,330 A * | 2/1987 | Dowling | 340/575 |
| 4,666,198 A | 5/1987 | Heiserman | |
| 4,669,477 A | 6/1987 | Ober | |
| 4,700,203 A | 10/1987 | Yamamuro et al. | |
| 4,715,367 A | 12/1987 | Crossley | |
| 4,747,413 A | 5/1988 | Bloch | |
| 4,748,672 A | 5/1988 | Nevill, Jr. et al. | |
| 4,788,533 A | 11/1988 | Mequignon | |
| 4,791,933 A | 12/1988 | Asai et al. | |
| 4,813,427 A | 3/1989 | Schlaefke et al. | |
| 4,814,661 A | 3/1989 | Ratzlaff et al. | |
| 4,817,625 A | 4/1989 | Miles | |
| 4,819,860 A | 4/1989 | Hargrove et al. | |
| 4,823,802 A | 4/1989 | Romanovskaya | |
| 4,827,943 A | 5/1989 | Bornn et al. | |
| 4,830,008 A | 5/1989 | Meer | |
| 4,834,109 A | 5/1989 | Watson | |
| 4,836,219 A | 6/1989 | Hobson et al. | |
| 4,895,160 A | 1/1990 | Reents | |
| 4,909,260 A | 3/1990 | Salem et al. | |
| 4,958,645 A | 9/1990 | Cadell et al. | |
| 4,960,118 A | 10/1990 | Pennock | |
| 4,971,065 A | 11/1990 | Pearce | |
| 4,986,277 A | 1/1991 | Sackner | |
| 4,989,612 A | 2/1991 | Fore | |
| 5,038,785 A | 8/1991 | Blakeley et al. | |
| 5,069,221 A | 12/1991 | Smith et al. | |
| 5,088,501 A | 2/1992 | Niewisch | |
| 5,099,702 A | 3/1992 | French | |
| 5,113,566 A | 5/1992 | Weekamp et al. | |
| 5,123,425 A | 6/1992 | Shannon, Jr. et al. | |
| 5,161,541 A | 11/1992 | Bowman et al. | |
| 5,178,156 A | 1/1993 | Takishima et al. | |
| 5,201,322 A | 4/1993 | Henry et al. | |
| 5,207,230 A | 5/1993 | Bowers | |
| D338,413 S | 8/1993 | Ciambella | |
| 5,277,193 A | 1/1994 | Takishima et al. | |
| 5,295,490 A | 3/1994 | Dodakian | |
| 5,311,875 A | 5/1994 | Stasz | |
| 5,329,931 A | 7/1994 | Clauson et al. | |
| 5,331,968 A | 7/1994 | Williams et al. | |
| 5,335,657 A | 8/1994 | Terry, Jr. et al. | |
| 5,348,008 A | 9/1994 | Bornn et al. | |
| 5,365,937 A | 11/1994 | Reeves et al. | |
| 5,413,111 A | 5/1995 | Wilkinson | |
| 5,477,867 A | 12/1995 | Balkanyi | |
| 5,515,738 A | 5/1996 | Tamori | |
| 5,540,733 A | 7/1996 | Testerman et al. | |
| 5,549,655 A | 8/1996 | Erickson | |
| 5,555,891 A | 9/1996 | Eisenfeld | |
| 5,558,099 A | 9/1996 | Bowman et al. | |
| 5,748,103 A | 5/1998 | Flach et al. | |
| 5,762,583 A * | 6/1998 | Adams et al. | 600/25 |
| 5,765,563 A | 6/1998 | Schaaf | |
| 5,767,791 A | 6/1998 | Stoop et al. | |
| 5,797,849 A | 8/1998 | Vesely et al. | |
| 5,825,119 A | 10/1998 | Shibata et al. | |
| 5,825,293 A | 10/1998 | Ahmed et al. | |
| 5,827,198 A | 10/1998 | Kassal | |
| 5,832,592 A | 11/1998 | Bowman et al. | |
| 5,853,005 A | 12/1998 | Scanlon | |
| D410,584 S | 6/1999 | Stasz et al. | |
| 5,913,815 A * | 6/1999 | Ball et al. | 600/25 |
| 5,913,829 A | 6/1999 | Reeves et al. | |
| 5,924,979 A | 7/1999 | Swedlow et al. | |
| 5,963,650 A | 10/1999 | Simionescu et al. | |
| D417,161 S | 11/1999 | Stasz et al. | |
| 5,996,418 A | 12/1999 | Rector et al. | |
| 6,004,269 A * | 12/1999 | Crowley et al. | 600/439 |
| 6,070,098 A | 5/2000 | Moore-Ede et al. | |
| 6,091,973 A | 7/2000 | Colla et al. | |
| 6,093,158 A | 7/2000 | Morris | |
| 6,142,950 A | 11/2000 | Allen et al. | |
| 6,185,452 B1 | 2/2001 | Schulman et al. | |
| 6,213,942 B1 | 4/2001 | Flach et al. | |
| 6,213,955 B1 | 4/2001 | Karakasoglu et al. | |
| 6,240,316 B1 | 5/2001 | Richmond et al. | |
| 6,240,323 B1 | 5/2001 | Calenzo, Sr. et al. | |
| 6,251,126 B1 | 6/2001 | Ottenhoff et al. | |
| 6,254,545 B1 | 7/2001 | Stasz et al. | |
| 6,269,269 B1 | 7/2001 | Ottenhoff et al. | |
| 6,287,264 B1 | 9/2001 | Hoffman | |
| 6,306,088 B1 | 10/2001 | Krausman et al. | |
| 6,341,230 B1 | 1/2002 | Koike et al. | |
| 6,345,202 B2 | 2/2002 | Richmond et al. | |
| 6,363,270 B1 | 3/2002 | Colla et al. | |
| 6,368,287 B1 | 4/2002 | Hadas | |
| 6,383,143 B1 | 5/2002 | Rost | |
| 6,456,887 B1 | 9/2002 | Dudding et al. | |
| 6,485,432 B1 | 11/2002 | Stasz et al. | |
| 6,491,642 B1 | 12/2002 | Stasz | |
| 6,496,705 B1 | 12/2002 | Ng et al. | |
| 6,544,192 B2 | 4/2003 | Starr et al. | |
| 6,544,199 B1 | 4/2003 | Morris | |
| 6,551,256 B1 | 4/2003 | Stasz et al. | |
| 6,561,987 B2 | 5/2003 | Pail | |
| 6,702,755 B1 | 3/2004 | Stasz et al. | |
| 6,734,802 B2 | 5/2004 | Halleck et al. | |
| 6,762,687 B2 | 7/2004 | Perlman | |
| 6,811,538 B2 | 11/2004 | Westbrook et al. | |
| 6,840,907 B1 | 1/2005 | Brydon | |
| 6,894,427 B2 | 5/2005 | Alfini | |
| 6,935,335 B1 | 8/2005 | Lehrman et al. | |
| 7,007,177 B2 | 2/2006 | Cannon et al. | |
| 7,089,932 B2 | 8/2006 | Dodds | |
| 7,115,097 B2 | 10/2006 | Johnson | |
| 7,134,435 B2 | 11/2006 | Scott | |
| 7,206,639 B2 * | 4/2007 | Jacobsen et al. | 607/57 |
| 7,267,652 B2 | 9/2007 | Coyle et al. | |
| 7,277,749 B2 | 10/2007 | Gordon et al. | |
| 7,322,356 B2 | 1/2008 | Critzer et al. | |
| 7,336,991 B2 | 2/2008 | Yanagihara et al. | |
| 7,363,926 B2 | 4/2008 | Pflueger et al. | |
| 7,367,935 B2 | 5/2008 | Mechlenburg et al. | |
| 7,422,014 B1 | 9/2008 | Smith | |
| 7,426,412 B1 | 9/2008 | Schecter | |
| 7,427,270 B2 | 9/2008 | Izumi et al. | |
| 7,524,279 B2 * | 4/2009 | Auphan | 600/26 |
| 2001/0018547 A1 | 8/2001 | Mechlenburg et al. | |
| 2002/0057202 A1 | 5/2002 | Luzon | |
| 2002/0123692 A1 | 9/2002 | Pail | |
| 2003/0100843 A1 | 5/2003 | Hoffman | |
| 2003/0187356 A1 | 10/2003 | Wakabayashi et al. | |
| 2003/0195588 A1 | 10/2003 | Fischell et al. | |
| 2003/0236467 A1 | 12/2003 | Alfini | |
| 2004/0039419 A1 | 2/2004 | Stickney et al. | |
| 2004/0113771 A1 | 6/2004 | Ozaki et al. | |
| 2004/0182386 A1 | 9/2004 | Meier | |
| 2004/0193003 A1 | 9/2004 | Mechlenburg et al. | |
| 2005/0061315 A1 | 3/2005 | Lee et al. | |
| 2005/0113646 A1 | 5/2005 | Sotos et al. | |
| 2005/0124864 A1 | 6/2005 | Mack et al. | |
| 2005/0137464 A1 | 6/2005 | Bomba | |
| 2005/0261559 A1 | 11/2005 | Mumford et al. | |
| 2006/0000472 A1 | 1/2006 | Fenton | |
| 2006/0034348 A1 | 2/2006 | Schaefer et al. | |
| 2006/0069320 A1 | 3/2006 | Wolff et al. | |
| 2006/0102171 A1 | 5/2006 | Gavish | |
| 2006/0145878 A1 | 7/2006 | Lehrman et al. | |
| 2006/0206014 A1 | 9/2006 | Ariav | |
| 2006/0212273 A1 | 9/2006 | Krausman et al. | |
| 2006/0212745 A1 | 9/2006 | Zansky et al. | |
| 2006/0214507 A1 | 9/2006 | Suzuki | |
| 2006/0241708 A1 | 10/2006 | Boute | |

(56) References Cited

U.S. PATENT DOCUMENTS

| | | |
|---|---|---|
| 2006/0283446 A1 | 12/2006 | Chua et al. |
| 2007/0012089 A1 | 1/2007 | Stasz |
| 2007/0016089 A1 | 1/2007 | Fischell et al. |
| 2007/0049842 A1 | 3/2007 | Hill et al. |
| 2007/0123758 A1 | 5/2007 | Miesel et al. |
| 2007/0129644 A1 | 6/2007 | Richards et al. |
| 2007/0131231 A1 | 6/2007 | Sharp |
| 2007/0154022 A1 | 7/2007 | Iketani et al. |
| 2007/0161903 A1 | 7/2007 | Yamashita et al. |
| 2007/0172029 A1 | 7/2007 | Felmlee et al. |
| 2007/0249952 A1 | 10/2007 | Rubin et al. |
| 2007/0255161 A1 | 11/2007 | De Backer |
| 2007/0282212 A1 | 12/2007 | Sierra et al. |
| 2007/0282215 A1 | 12/2007 | Ni et al. |
| 2008/0009915 A1 | 1/2008 | Moses et al. |
| 2008/0021506 A1 | 1/2008 | Grocela |
| 2008/0035158 A1 | 2/2008 | Pflueger et al. |
| 2008/0066753 A1 | 3/2008 | Martin et al. |
| 2008/0082018 A1 | 4/2008 | Sackner et al. |
| 2008/0092898 A1 | 4/2008 | Schneider et al. |
| 2008/0103407 A1 | 5/2008 | Bolea et al. |
| 2008/0103545 A1 | 5/2008 | Bolea et al. |
| 2008/0221468 A1 | 9/2008 | Stahmann et al. |
| 2008/0234780 A1 | 9/2008 | Smith et al. |
| 2008/0236597 A1 | 10/2008 | Bergersen |
| 2008/0243014 A1 | 10/2008 | Moussavi et al. |
| 2008/0243017 A1 | 10/2008 | Moussavi et al. |
| 2008/0243023 A1 | 10/2008 | Valkhof et al. |
| 2008/0275356 A1 | 11/2008 | Stasz et al. |
| 2009/0050154 A1 | 2/2009 | Strothmann et al. |
| 2009/0076405 A1 | 3/2009 | Amurthur et al. |
| 2009/0158425 A1 | 6/2009 | Chan et al. |
| 2009/0306528 A1 | 12/2009 | Curti et al. |
| 2010/0048985 A1 | 2/2010 | Henke et al. |
| 2010/0048986 A1 | 2/2010 | Henke et al. |
| 2010/0049264 A1 | 2/2010 | Henke et al. |
| 2010/0049265 A1 | 2/2010 | Henke et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0063348 A1 | 3/2010 | Henke et al. |
| 2010/0063350 A1 | 3/2010 | Henke et al. |
| 2010/0069769 A1 | 3/2010 | Henke et al. |
| 2010/0069771 A1 | 3/2010 | Henke et al. |
| 2010/0069772 A1 | 3/2010 | Henke et al. |
| 2010/0069773 A1 | 3/2010 | Henke et al. |
| 2010/0076251 A1 | 3/2010 | Stasz |
| 2010/0076252 A1 | 3/2010 | Henke et al. |

FOREIGN PATENT DOCUMENTS

| | | |
|---|---|---|
| EP | 1745742 A1 | 1/2007 |
| WO | WO-9705824 A1 | 2/1997 |
| WO | WO-0143804 A1 | 6/2001 |
| WO | WO-03022149 A2 | 3/2003 |
| WO | WO-03082108 A1 | 10/2003 |
| WO | WO-2004112606 A1 | 12/2004 |
| WO | WO-2006066337 A1 | 6/2006 |
| WO | WO-2006116469 A3 | 11/2006 |
| WO | WO-2007008706 A3 | 1/2007 |
| WO | WO-2007071180 A1 | 6/2007 |
| WO | WO-2008037820 A1 | 4/2008 |
| WO | WO-09134434 A1 | 11/2009 |
| WO | WO-2010021730 A1 | 2/2010 |
| WO | WO-2010030909 A1 | 3/2010 |
| WO | WO-2010033819 A1 | 3/2010 |
| WO | WO-2010033849 A1 | 3/2010 |

OTHER PUBLICATIONS

"European Application Serial No. 09739237.7, Examination Notification Art. 94(3) mailed Jun. 20, 2011", 5.

"International Application Serial No. PCT/US2009/002705, Search Report mailed Oct. 1, 2009".

"International Application Serial No. PCT/US2009/002705, Written Opinion mailed Oct. 1, 2009".

"U.S. Appl. No. 12/583,589, Response filed Apr. 5, 2012 to Restriction Requirement mailed Feb. 6, 2012", 7 pgs.

"U.S. Appl. No. 12/491,068, Notice of Allowance mailed Nov. 28, 2011", 17 pgs.

"U.S. Appl. No. 12/547,167, Non Final Office Action mailed Nov. 7, 2011", 5 pgs.

"U.S. Appl. No. 12/547,167, Notice of Allowance mailed Dec. 28, 2011", 5 pgs.

"U.S. Appl. No. 12/547,167, Response filed Nov. 8, 2011 to Non Final Office Action mailed Nov. 7, 2011", 11 pgs.

"U.S. Appl. No. 12/557,765, Non Final Office Action mailed Mar. 9, 2012", 16 pgs.

"U.S. Appl. No. 12/557,765, Response filed Feb. 23, 2012 to Restriction Requirement mailed Dec. 23, 2011", 8 pgs.

"U.S. Appl. No. 12/557,765, Restriction Requirement mailed Dec. 23, 2011", 5 pgs.

"U.S. Appl. No. 12/557,777, Non Final Office Action mailed Feb. 2, 2012", 19 pgs.

"U.S. Appl. No. 12/557,790, Non Final Office Action mailed Dec. 22, 2011", 11 pgs.

"U.S. Appl. No. 12/557,790, Response filed May 22, 2012 to Non Final Office Action mailed Dec. 22, 2011", 8 pgs.

"U.S. Appl. No. 12/558,104, Non Final Office Action Mailed Feb. 3, 2012", 17 pgs.

"U.S. Appl. No. 12/562,959 Response filed May 21, 2012 to Restriction Requirement mailed Apr. 19, 2012", 6 pgs.

"U.S. Appl. No. 12/562,959, Restriction Requirement mailed Apr. 19, 2012", 5 pgs.

"U.S. Appl. No. 12/583,589, Restriction Requirements mailed Feb. 6, 2012", 8 pgs.

"U.S. Appl. No. 12/583,591, Non Final Office Action mailed Mar. 30, 2012", 11 pgs.

"European Application Serial No. 09739237.7, Response filed Apr. 18, 2012 to Office Action mailed Jun. 20, 2011", 4 pgs.

"International Application Serial No. PCT/US2009/002230, International Search Report mailed Jul. 3, 2009", 6 pgs.

"International Application Serial No. PCT/US2009/002230, Written Opinion mailed Jul. 3, 2009", 6 pgs.

"International Application Serial No. PCT/US2009/002408, Search Report mailed Aug. 13, 2009", 7 pgs.

"International Application Serial No. PCT/US2009/002408, Written Opinion mailed Aug. 13, 2009," 6 pgs.

"International Application Serial No. PCT/US2009/002705, International Preliminary Report on Patentability mailed", 7 pgs.

"International Application Serial No. PCT/US2009/004766, International Report on Patentability mailed Mar. 3, 2011", 8 pgs.

"International Application Serial No. PCT/US2009/004766, Search Report mailed Jan. 26, 2010", 7 pgs.

"International Application Serial No. PCT/US2009/004766, Written Opinion mailed Jan. 26, 2010", 6 pgs.

"International Application Serial No. PCT/US2009/048491, International Preliminary Report on Patentability mailed Jan. 5, 2011", 8 pgs.

"International Application Serial No. PCT/US2009/048491, International Search Report and Written Opinion mailed Sep. 28, 2009", 11 pgs.

"International Application Serial No. PCT/US2009/056697, International Preliminary Report on Patentability mailed Mar. 24, 2011", 7 pgs.

"International Application Serial No. PCT/US2009/056697, Search Report mailed Nov. 25, 2009", 4 pgs.

"International Application Serial No. PCT/US2009/056697, Written Opinion mailed Nov. 25, 2009", 5 pgs.

"International Application Serial No. PCT/US2009/057499, Search Report mailed Feb. 8, 2010", 8 pgs.

"International Application Serial No. PCT/US2009/057499, Written Opinion mailed Feb. 8, 2010", 9 pgs.

(56) References Cited

OTHER PUBLICATIONS

"International Application Serial No. PCT/US2009/057546, International Preliminary Report on Patentability mailed Mar. 31, 2011", 9 pgs.

"International Application Serial No. PCT/US2009/057546, Search Report mailed Dec. 30, 2009", 8 pgs.

"International Application Serial No. PCT/US2009/057546, Written Opinion mailed Dec. 30, 2009", 8 pgs.

"Piezo Film Sensors Technical Manual passage", Piezo Film Sensors Technical Manual, Measurement Specialties inc. No. 1005663-1 Rev. B, XP007906698 p. 11, line 1-line 31, (Apr. 2, 1999), 89 pgs.

Jovanov, E., et al., "Patient monitoring using personal area networks of wireless intelligent sensors", Bio-medical Sciences Instrumentation; vol. 37, XP002554091 ISSN: 0067-8856, (2001), 6 pgs.

Jovanov, E., et al., "Thermistor-based breathing sensor for circadian rhythm evaluation", Bio-medical Sciences Instrumentation; vol. 37, XP002554092 ISSN: 0067-8856, (2001), 5 pgs.

"U.S. Appl. No. 12/557,765, Response filed Jul. 9, 2012 to Non Final Office Action mailed Mar. 9, 2012", 14 pgs.

"U.S. Appl. No. 12/557,765, Final Office Action mailed Aug. 2, 2012", 17 pgs.

"U.S. Appl. No. 12/557,777, Final Office Action mailed Aug. 8, 2012", 21 pgs.

"U.S. Appl. No. 12/557,777, Response filed Jul. 2, 2012 to Non Final Office Action mailed Feb. 2, 2012", 13 pgs.

"U.S. Appl. No. 12/558,104, Response filed Jul. 13, 2012 to Non Final Office Action mailed Feb. 3, 2012", 12 pgs.

"U.S. Appl. No. 12/562,669, Non Final Office Action mailed Aug. 28, 2012", 8 pgs.

"U.S. Appl. No. 12/562,959, Non Final Office Action mailed Aug. 23, 2012", 8 pgs.

"U.S. Appl. No. 12/583,580, Restriction Requirement mailed Dec. 17, 2012", 7 pgs.

"U.S. Appl. No. 12/583,582, Restriction Requirement mailed Dec. 18, 2012", 7 pgs.

"U.S. Appl. No. 12/583,588, Non Final Office Action mailed Jun. 29, 2012", 9 pgs.

"U.S. Appl. No. 12/583,591, Final Office Action mailed Dec. 14, 2012", 11 pgs.

"U.S. Appl. No. 12/583,591, Response filed Aug. 30, 2012 to Non Final Office Action mailed Mar. 30, 2012", 14 pgs.

\* cited by examiner

AGITATOR TO STIMULATE THE CENTRAL NERVOUS SYSTEM

CLAIM OF PRIORITY

This patent application claims the benefit of priority to U.S. Provisional Patent Application Ser. No. 61/049,802, filed on May 2, 2008, which application is herein incorporated by reference in its entirety.

TECHNICAL FIELD

This invention relates generally to the field of neurological disorders and more specifically to the area of sleep medicine and yet even more specifically to the area of sleep therapy for patients who suffer from sleep disorders such as obstructive sleep apnea, central sleep apnea, complex sleep apnea, restless leg syndrome (RLS), sudden infant death syndrome (SIDS) and related physiologic events or conditions occurring during sleep. More particularly, the present invention relates to a device for stimulating the central nervous system of a patient suffering from a sleep disorder.

BACKGROUND

Sleep disorders have recently become the focus of a growing number of physicians. Many hospitals and clinics have established sleep laboratories (sleep labs) to diagnose and treat sleep disorders. In the sleep laboratories, practitioners use instrumentation to monitor and record a patient's sleep states and behaviors during sleep. Practitioners rely on these recordings to diagnose patients and prescribe proper therapies.

Various undesirable behaviors can occur during sleep, such as snoring, apnea episodes, abnormal breathing episodes and the like. In certain examples, these and other undesirable behaviors can lead to insufficient amounts of sleep, fatigue, or in the case of SIDS, even death. Thus, efforts are being made to reduce or eliminate these undesirable behaviors.

SUMMARY

In an example, a tactile and audible sensation can be provided to a patient using a coiled or scrolled film in response to a received control signal. In certain examples, the tactile and audible sensation can be configured to stimulate the patient's central nervous system to sufficiently interrupt and undesirable sleep behavior of the patient, but avoid significantly changing a sleep state of the patient.

In other examples, an agitator device can include a coiled film within a housing, the housing being in contact with a sleep patient, wherein the coiled film is connected to a selective source of alternating current, which matches the resonant frequency of the film such that when activated the film rapidly expands and contracts creating a mechanical motion or vibration, which creates a tactile event which is detected by the central nervous system of the sleep patient and wherein undesired sleeping behavior is interrupted, but sleep states are not altered nor is the patient awakened. The film is further disclosed as a piezoelectric film or a polyvinylidene film with metalized opposing surfaces. Further disclosed is a central nervous system stimulation controller controlling the signal transmitted to the agitator device.

Various stimulation systems are available for altering undesirable behavior during sleeping. For example, several United States patents are directed toward treatment of snoring including U.S. Pat. No. 4,644,330 to Dowling, U.S. Pat. No. 4,788,533 to Mequignon, and U.S. Pat. No. 5,477,867 to Balkanyi. These patents rely on an "aversive audio stimulus," a "sound stimulus," and "acoustic signals," respectively.

As another example, in U.S. Pat. No. 3,802,417 to Lang, an alarm relay is triggered if a desired standard respiratory frequency is not attained. When triggered, the alarm relay switches on a respiration stimulator that consists of a rhythmically inflatable belt or cuff.

As an additional example, U.S. Pat. No. 4,715,367 to Crossley discloses a device to diagnose, treat and monitor treatment for snoring, bruxism, or sleep apnea. Here, treatment consists of a regulatable aversive shock.

As an additional example, U.S. Pat. No. 6,093,158 to Morris discloses monitoring an undesired behavioral disorder such as bruxism, jaw clenching, or snoring. Here, an alert system is selected from a group consisting of light controllers, temperature regulators, odor generators, high frequency generators, tactile pressure generators, vibratory generators, and electric current generators.

Further yet, U.S. Pat. No. 6,935,335 to Lehrman et al. discloses creating a stimulus to a person's neck muscles to cause said person to move said person's neck muscles to move said person's head backwards to terminate said physiological process before cessation of breathing occurs. The stimulus includes a vibrator and a sound generator placed adjacent to said person's neck muscles. Additional examples can be found in U.S. Patent Publication No. US 2003/0,195,588 to Fischell et al. and US 2008/0,009,915 to Moses et al.

The goal of addressing sleeping disorders is often to help a person sleep better. Several states of sleep exist and involve varying levels of consciousness, and the beneficial effects of sleep improve when it is uninterrupted. To the extent that devices above alter a patient's sleep state, or in a worst case scenario actually awaken a patient, the devices have gone too far. While they may have stopped the undesirable behavior, they have not helped a person sleep better.

In light of this very fine line between interrupting an undesirable behavior and altering a sleep state, there are several problems associated with the above devices. First, in the case of the audio, light, or odor devices, a vast range of patient sensitivities exist for each of these stimuli. Thus, these devices can have difficulty simultaneously altering an undesirable behavior and avoiding alteration of a sleep state because they are often under or over effective at stimulating a patient. Second, the inflatable belt or cuff and the temperature regulator both involve a certain ramp up and shut down time. This can make it difficult to precisely dose a patient when trying to stimulate the patient at the instant an undesirable behavior starts and to stop stimulation at the instant the behavior stops. Third, regarding the electric current and aversive shock, many people simply are not comfortable with the nature of this treatment. Fourth, vibration can work fairly universally, however, due to the inertial forces involved, the devices tend to have the same shut down problems mentioned above. That is, once the undesirable behavior stops and the device is switched off, it takes time for the vibration to stop and thus stop stimulating the patient. This can lead to over stimulation and an alteration in the patient's sleep state.

The present inventor has realized, among other things, that there is a need to provide an apparatus and method that stimulates the central nervous system sufficiently to interrupt an undesirable sleep behavior by a means universally sensed by most patients where the device avoids significantly changing sleep states and avoids waking a patient. Moreover, there is a need for this apparatus to be precisely controllable so as to provide precise doses of stimulation to a sleep disorder patient. There is also a need to provide an apparatus that is comfortable to wear so as to further its ability to avoid alteration of sleep states.

Certain embodiments of the present invention provide a piezoelectric agitation device that, by means of piezoelectric to mechanical motion conversion, provides stimulation of the central nervous system in general and to the human central nervous system in specific by means of tactical stimulation, by means of audible stimulation, or by both tactile and audio stimulation.

In one embodiment, a small strip of metalized piezoelectric film, preferably of either series or parallel bimorphic structure with wire terminals attached to opposing metalized surfaces of the film, has a coil, scroll, or barrel shape and is situated within a small plastic, glass, metal, or composite housing.

In another embodiment, a small strip of polyvinylidene fluoride film, with wire terminals attached to opposing metalized surfaces, has the shape of a loosely rolled scroll and is situated within a housing.

In Example 1, an agitator device for stimulating a central nervous system of a patient suffering from a sleep disorder includes a housing sized and shaped to fit within, on, around, or behind an ear of the patient, a film within the housing, the film configured to receive a control signal and to provide a tactile and audible sensation to the patient in response to the received control signal, the tactile and audible sensation configured to stimulate the patient's central nervous system to sufficiently interrupt an undesirable sleep behavior of the patient, but avoid significantly changing a sleep state of the patient.

In Example 2, the film of Example 1 optionally includes a coiled or scrolled polyvinylidene fluoride (PVDF) film.

In Example 3, the PVDF film of any one or more of Examples 1-2 optionally includes a metalized PVDF film having at least one of a series or parallel bimorphic structure.

In Example 4, the housing of any one or more of Examples 1-3 is optionally configured to fit within the ear.

In Example 5, the control signal of any one or more of Examples 1-4 optionally includes an alternating current (AC) excitation voltage control signal configured to control expansion and contraction of the film according to an instantaneous voltage polarity of the control signal, causing the film to vibrate, the vibration providing the tactile and audible sensation.

In Example 6, the frequency of the control signal of any one or more of Examples 1-5 is optionally configured to substantially match a resonant frequency of the film to provide a desired efficiency of the tactile and audible sensation.

In Example 7, the frequency of the control signal of any one or more of Examples 1-6 optionally includes a frequency between 1 Hz and 100 Hz.

In Example 8, a system for stimulating a central nervous system of a patient suffering from a sleep disorder includes a sleep sensor configured to receive sleep information from the patient, an agitator including a housing sized and shaped to fit within, on, around, or behind an ear of the patient and a film within the housing, the film configured to provide a tactile and audible sensation to the patient, the tactile and audible sensation configured to stimulate the patient's central nervous system, and a controller configured to receive sleep information from the sleep sensor, to produce a control signal for the agitator using the received sleep information, and to provide the control signal to the to the agitator, the control signal configured to control the tactile and audible sensation of the agitator to sufficiently interrupt an undesirable sleep behavior of the patient, but avoid significantly changing a sleep state of the patient.

In Example 9, the sleep sensor of Example 8 optionally includes a respiration sensor configured to receive respiration information from the patient.

In Example 10, the sleep sensor of any one or more of Examples 8-9 optionally includes a sleep state sensor configured to receive information indicative of a sleep state of the patient.

In Example 11, the film of any one or more of Examples 8-10 optionally includes a coiled or scrolled metalized polyvinylidene fluoride (PVDF) film having at least one of a series or parallel bimorphic structure.

In Example 12, the housing of any one or more of Examples 8-11 is optionally configured to be affixed behind the ear using an adhesive.

In Example 13, the controller of any one or more of Examples 8-13 is optionally configured to produce an alternating current (AC) excitation voltage control signal to control expansion and contraction of the film according to an instantaneous voltage polarity of the control signal, causing the film to vibrate, the vibration providing the tactile and audible sensation, and wherein the frequency of the AC excitation voltage control signal is configured to substantially match a resonant frequency of the film to provide a desired efficiency of the tactile and audible sensation.

In Example 14, a method for stimulating a central nervous system of a patient suffering from a sleep disorder includes receiving a control signal from a controller and providing a tactile and audible sensation to the patient using a coiled or scrolled film in response to the received control signal, the tactile and audible sensation configured to stimulate the patient's central nervous system to sufficiently interrupt an undesirable sleep behavior of the patient, but avoid significantly changing a sleep state of the patient.

In Example 15, the method of Example 14 optionally includes receiving sleep information from a patient, the sleep information including at least one of respiration information of the patient from a respiration sensor or information indicative of a sleep state of the patient from a sleep state sensor, and producing the control signal using the received sleep information.

In Example 16, the receiving the sleep information from the patient of any one or more of Examples 14-15 optionally includes receiving the respiration information of the patient from the respiration sensor.

In Example 17, the providing the tactile and audible sensation to the patient using the coiled or scrolled film includes using a metalized polyvinylidene fluoride (PVDF) film having at least one of a series or parallel bimorphic structure.

In Example 18, the method of any one or more of Examples 14-17 optionally includes providing a housing sized and shaped to fit within, on, around, or behind an ear of the patient, the housing including the coiled or scrolled film.

In Example 19, the method of any one or more of Examples 14-18 optionally includes producing an alternating current (AC) excitation voltage control signal to control expansion and contraction of the coiled or scrolled film according to an instantaneous voltage polarity of the control signal.

In Example 20, the producing the AC excitation voltage control signal of any one or more of Examples 14-19 optionally includes at a frequency configured to substantially match a resonant frequency of the coiled or scrolled film to provide a desired efficiency of the provided tactile and audible sensation.

While the present disclosure is directed toward treatment of sleep disorders, further areas of applicability will become apparent from the description provided herein. It should be understood that the description and specific examples are intended for purposes of illustration only and are not intended to limit the scope of the present disclosure.

DESCRIPTION OF THE DRAWINGS

The forgoing features, objects and advantages of the invention will become apparent to those skilled in the art from the following detailed description, especially when considered in conjunction with the accompanying drawings in which like the numerals in the several views refer to the corresponding parts.

DETAILED DESCRIPTION

The following detailed description relates to an agitator directed toward treating patients with sleep disorders in sleep laboratories. The agitator is more particularly directed at stimulating a patient to interrupt and terminate an undesired sleep behavior or condition such as snoring, sleep apnea, sudden infant death syndrome (SIDS) and others. The agitator may be used in conjunction with a sensor affixed to a patient and a controller. The sensor transmits respiratory information to a controller that analyzes the information and may trigger the agitator depending on the information received.

The following detailed description includes discussion of sensors affixed to patients, controllers, and agitators. Additionally, elements of an agitator are discussed including a housing, a film, and wire terminations. Controller circuitry, a bridge amplifier, and a power supply are also discussed. Information regarding the wave form generated by the bridge amplifier is also included.

The present invention can be readily understood from FIGS. 1 through 8.

Figure 1:
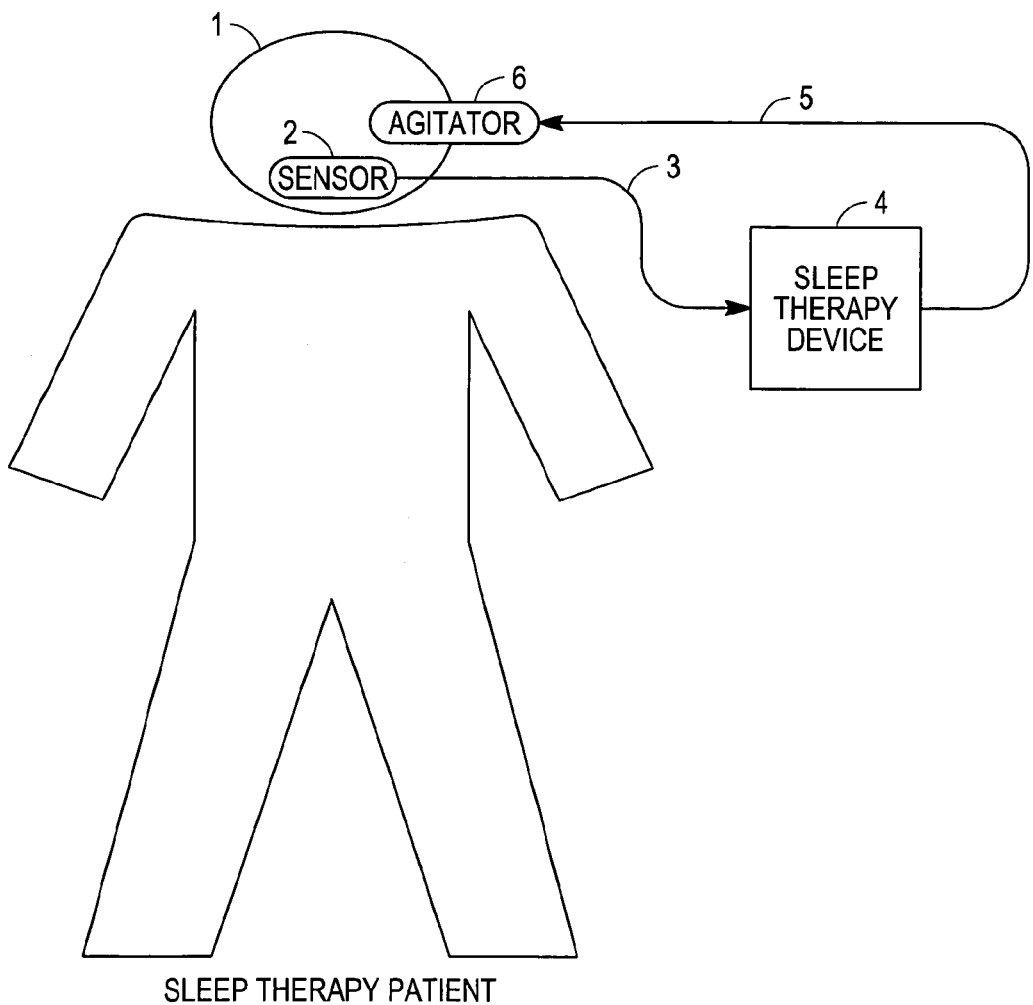
FIG. 1 illustrates generally an example of a system including an agitator.

FIG. 1 illustrates generally an example of a system including an agitator 6. In an example, a sleep therapy patient 1 suffering from a sleep disorder can be outfitted with a sensor 2 to measure respiratory effort. A pair of sensor output wire leads 3 connects the sensor to the input of the controller device 4. The output of the controller 4 connects via a pair of wire leads 5 to the agitator 6.

In an example, the sensor 2 of FIG. 1 can include a piezoelectric sensor constructed in accordance with the teachings of U.S. Pat. Nos. 5,311,875 and 6,254,545 to Stasz, the teachings of which are hereby incorporated by reference. Those skilled in the art will understand and appreciate that various sensors are known including, but not limited to thermistors, air pressure transducers, respiratory plethysmography inductance (RIP) belts, microphones, or one or more other sleep sensors, and that these sensors are within the scope of the present subject matter.

In an example, the controller shown in FIG. 1 can include a Central Nervous System Stimulation Controller. Those skilled in the art will understand and appreciate that various controllers exist for monitoring patients, analyzing information, and transmitting a signal to another device based on that information.

Figure 2:
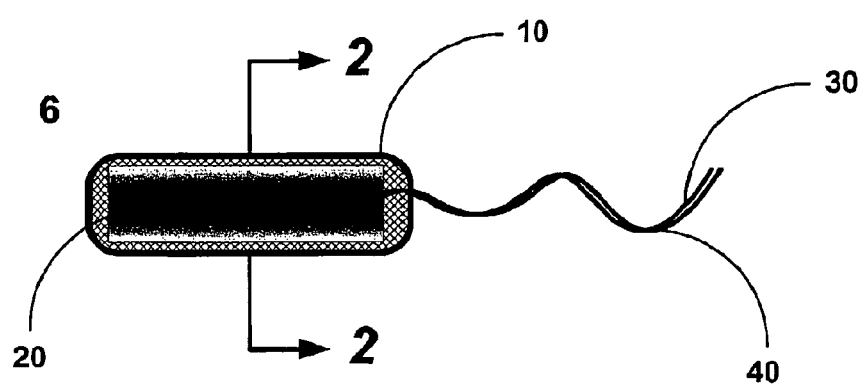
FIG. 2 illustrates generally an example of an agitator.

FIG. 2 illustrates generally an example of an agitator 6. In this example, there is indicated generally an agitator 6 along with a housing 10 containing a coiled or scrolled film 20. Attached to each surface of the film are wire terminations 30 and 40 via which the agitator receives the output from the controller and these devices are thus within the scope of the present invention.

Figure 3:
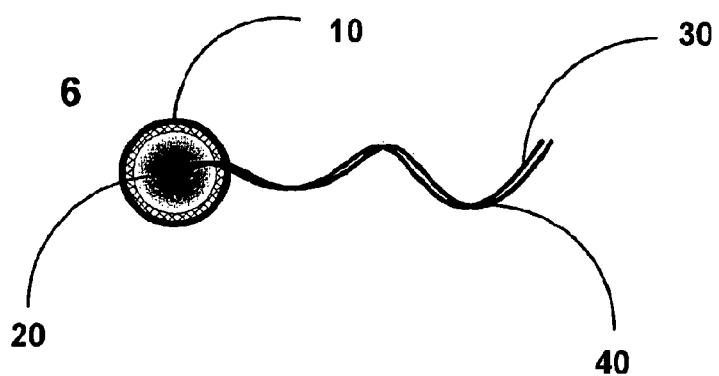
FIG. 3 illustrates generally an example of a cross-sectional view of an agitator.

FIG. 3 illustrates generally an example of a cross-sectional view of an agitator 6. In this example, there is indicated generally an agitator 6 along with housing 10 containing a coiled or scrolled film 20. Attached to each side of the film are the wire terminations 30 and 40 via which the agitator is connected to the controller.

Figure 4:
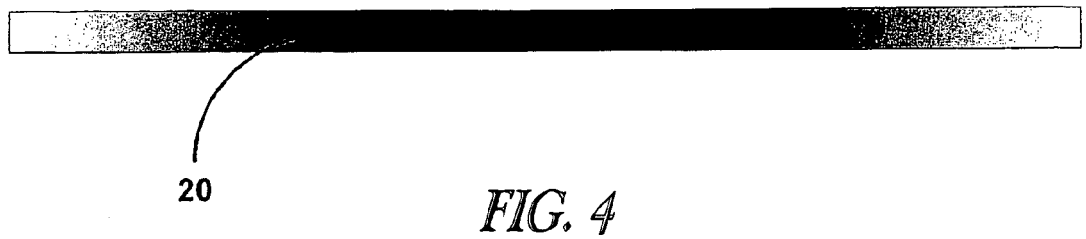
FIG. 4 illustrates generally an example of a rolled out (unscrolled) film.

FIG. 4 illustrates generally an example of a rolled out (unscrolled) film 20. Those skilled in the art will understand and appreciate that various lengths and widths of film are within the scope and spirit of the invention. The width and length can be varied based on several factors including but not limited to, the size of the device, the desired looseness of the fit of the film in the housing, and the desired level of agitation.

Figure 5:
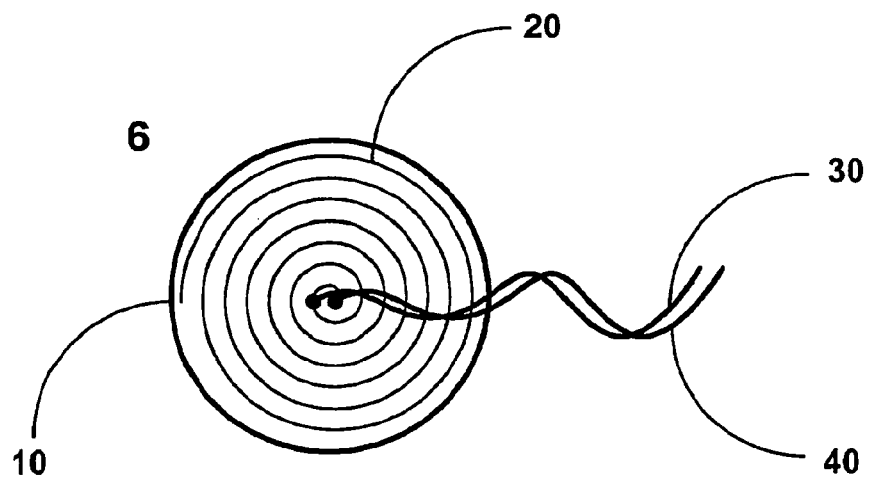
FIG. 5 illustrates generally an example of an agitator along with a housing containing a loosely coiled or scrolled up film.

FIG. 5 illustrates generally an example of an agitator 6 along with a housing 10 containing a loosely coiled or scrolled up film 20. Attached to each side of the film are wire terminations 30 and 40 via which the agitator 6 is connected to a controller.

In an example, the film shown in FIGS. 2-5 can include a piezoelectric film. More particularly, the film can include a polyvinylidene fluoride (PVDF) film. In certain examples, the PVDF film can be a metalized PVDF film of either series or parallel bimorphic structure. Those skilled in the art will understand and appreciate the piezoelectric to mechanical motion conversion properties of PVDF. However, other films known in the art which have mechanical motion conversion properties are within the scope of the invention. While the film is shown to be scrolled in the shape of a cylindrical coil, other shapes including square or triangular are within the scope of the invention.

The housing shown in FIGS. 2-5 can include a plastic, metal, glass, or composite material. In an example, the housing can be light weight so as to minimize the momentum associated with its motion. The housing could be any size and is not limited in size to use in conjunction with the human body. Moreover, the shape of the housing can vary and is not limited to a cylindrical shape. Other shapes including rectangular, triangular, or polygon shapes adapted for a specific purpose are within the scope of the invention. In an example, the shape of the housing may be adapted to fit within, on, around, or behind the ear similar to that of a hearing aid or ear bud. In other examples, the housing can be adapted to be fixed in, on, behind, or around the ear (e.g., using an adhesive).

In application, a controller can transmit an alternating current (AC) excitation voltage via wire terminations 30 and 40 to the opposing metalized surfaces of a PVDF film. The inherent characteristics of the loosely rolled piezoelectric film can cause it to expand and contract according to the instantaneously applied voltage polarity of the excitation signal, thus causing the film to vibrate. In an example, the frequency of the AC can match the resonance frequency of the coiled structure of the agitator thus minimizing the required electrical power and maximizing the resulting mechanical force. The AC current frequency, while not limited to this range, may fall in the range of 1 Hz to 100 Hz.

The resulting mechanical motion or vibration of the film can be transferred to the housing of the agitator which can creates both a tactile and audible sensation. This mechanical motion or vibration is passed subsequently on to the hairs and skin of the patient that the agitator is in contact with. This transfer of mechanical motion or vibration to the skin and hairs of the patient creates a tactile event which is detected by the central nervous system.

In one embodiment, as mentioned above, the housing can be in the shape of an ear bud for placement in a patient's ear. In this embodiment, the agitator creates a sensation comparable to an insect moving around quickly and briefly in the ear canal.

In an example embodiment, the stimulation of the agitator can be sufficient to cause a sleeping patient to interrupt an undesirable sleeping behavior, but is not sufficient to alter the sleep state of the patient. Thus, depending on the condition being treated, the patient can stop snoring, or start breathing without alteration of the patient's sleep state.

The nature of the thin film and light weight housing allows the device to maintain a low momentum even at high velocity. Thus, the ramp up and shut down period required for this device is almost instantaneous. When the AC excitation voltage is transmitted, the device immediately begins its mechanical motion or vibration and when the AC excitation voltage stops, the device immediately stops. This is because the momentum of the device, while moving very quickly, is small, because of its low mass. This is in contrast to well known vibratory devices in cell phones and pagers, where the mass of the devices is quite large relative to the agitator disclosed herein.

Figure 6:
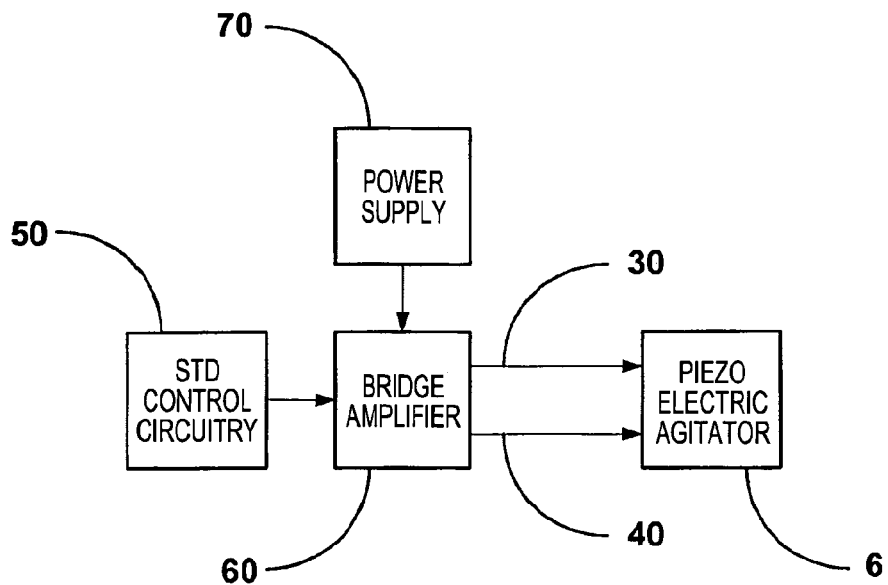
FIG. 6 illustrates generally an example of a block diagram of an electrical control circuit for producing a control signal for an agitator.

FIG. 6 illustrates generally an example of a block diagram of an electrical control circuit for producing a control signal for an agitator 6. In this example, the controller circuitry 50 is configured to issue the precisely dosed control signal for further processing in a typical high voltage bridge amplifier 60. In this example, the bridge amplifier 60 is powered by the power supply 70. The bridge amplifier 60 connects to the agitator 6 via the electrical wire pairs 30 and 40.

In one embodiment, the power supply 70 is a typical electrical power outlet. In another embodiment, the power supply is battery power. In yet another embodiment, as discussed in more detail below, the power supply for the controller is separate from the power supply for the agitator. In this embodiment, the power supply for each of them could be an electrical outlet or battery power.

Figure 7:
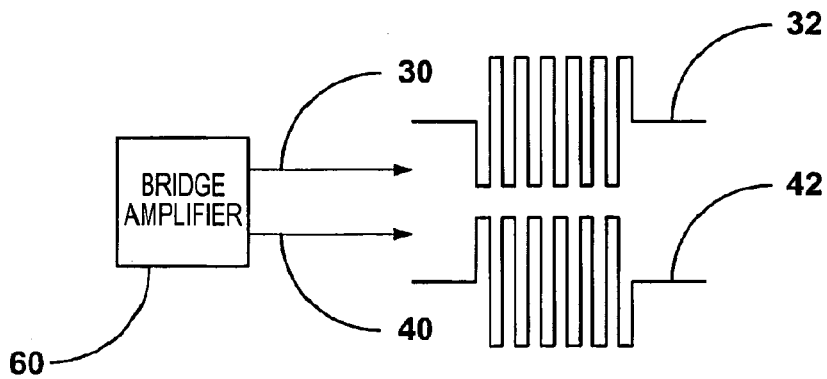
FIG. 7 illustrates generally an example of a high-energy piezoelectric agitator control waveform pair.

FIG. 7 illustrates generally an example of a high-energy piezoelectric agitator control waveform pair 32 and 42. In an example, the high-energy piezoelectric agitator control waveform pair 32 and 42 can be generated by the bridge amplifier 60 and carried to a piezoelectric agitator via the wire leads 30 and 40.

Figure 8:
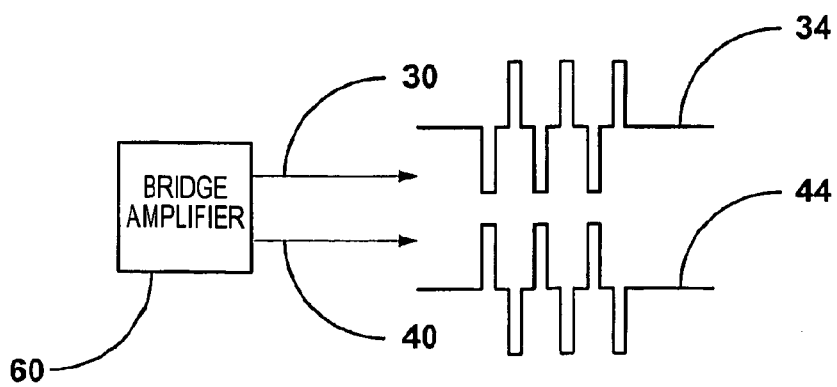
FIG. 8 illustrates generally an example of a low-energy piezoelectric agitator control waveform pair.

FIG. 8 illustrates generally an example of a low-energy piezoelectric agitator control waveform pair 34 and 44. In an example, the low-energy piezoelectric agitator control waveform pair 34 and 44 can be generated by the bridge amplifier 60 and carried to a piezoelectric agitator via the wire leads 30 and 40.

The energy of the waveform results in higher and lower levels of vibration magnitude. Those skilled in the art will understand and appreciate that various waveforms are available and the two shown are merely exemplary. Alternative waveforms include, but are not limited to, sinusoidal, square, trapezoidal, triangular, and sawtooth.

In one embodiment, a wireless agitator includes a housing, a receiver, a power supply, and a film located within the housing. During application, the receiver receives a remote signal from a controller and sends the signal to the film via wire terminations. The receiver is powered by the power supply. In an alternative embodiment, the remotely controlled agitator also includes a controller and may further include a bridge amplifier. In this embodiment, the receiver can receive a signal from either a transmitter on the patient sensor or from a transmitter connected to the patient sensor. In either case, the receiver can transmit the signal to the controller which in turn can transmit the signal to the bridge amplifier. As with the above embodiments, a waveform can then be transmitted to the film creating mechanical movement of the agitator.

The present inventor has realized, among other things, that an agitator can be directed toward transfer of mechanical energy to create a tactile sensation, which makes the device universally effective for most sleep patients. This is in contrast to the sound, light, and odor type devices of the prior art.

An additional advantage of the present invention is the precision with which stimulating doses can be given to a sleep patient. Due to the light weight nature of the device and its electrical activation, the device can be started and stopped extremely quickly thus stimulating the central nervous system in very specific and defined doses. This contributes to its ability to interrupt an undesired behavior and yet avoid altering the patients' sleep state.

Another advantage of the present invention relating to its light weight is the ability to cause large magnitude mechanical motion with very little electrical power simply by stimulating the device with an alternating current matching its resonant frequency. This advantage makes it possible for the device to be supplied with battery power and sustain battery life for an extended period of time.

This leads to an additional advantage. The device's ability to operate on battery power can allow the device to operate remotely, thus eliminating the need for wire leads and positive electrical connections to a controller. Thus, the device can be placed in the ear much like a hearing aid and be worn very comfortably by a sleep patient. This further supports the device's ability to interrupt an undesirable behavior while avoiding alteration of a sleep state.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

The description of the various embodiments is merely exemplary in nature and, thus, variations that do not depart from the gist of the examples and detailed description herein are intended to be within the scope of the present disclosure. Such variations are not to be regarded as a departure from the spirit and scope of the present disclosure.

What is claimed is:

1. A method for stimulating a central nervous system of a patient suffering from a sleep disorder, comprising:
   receiving a control signal from a controller;
   transferring a mechanical vibration of a coiled or scrolled film to a housing, sized and shaped to fit within, on, around, or behind an ear of the patient, in response to the received control signal, wherein the housing includes the coiled or scrolled film; and passing a tactile and audible sensation to the patient using the housing, the tactile and audible sensation configured to stimulate the patient's central nervous system to interrupt an undesirable sleep behavior of the patient, but avoid changing a sleep state of the patient.

2. The method of claim 1, including:
receiving sleep information from a patient, the sleep information including at least one of:
respiration information of the patient from a respiration sensor; or
information indicative of a sleep state of the patient from a sleep state sensor; and
producing the control signal using the received sleep information.

3. The method of claim 2, wherein the receiving the sleep information from the patient includes receiving the respiration information of the patient from the respiration sensor.

4. The method of claim 1, wherein the transferring a mechanical vibration of the coiled or scrolled film includes using a metalized polyvinylidene fluoride (PVDF) film having at least one of a series or parallel bimorphic structure.

5. The method of claim 1, including producing an alternating current (AC) excitation voltage control signal to control expansion and contraction of the coiled or scrolled film according to an instantaneous voltage polarity of the control signal.

6. The method of claim 5, wherein the producing the AC excitation voltage control signal includes producing the AC excitation voltage control signal at a frequency configured to match a resonant frequency of the coiled or scrolled film to provide a desired efficiency of the provided tactile and audible sensation.

7. The method of claim 1, wherein the film includes a coiled or scrolled polyvinylidene fluoride (PVDF) film.

8. The method of claim 7, wherein the PVDF film includes a metalized PVDF film having at least one of a series or parallel bimorphic structure.

9. The method of claim 1, wherein the film includes a coiled film.

10. The method of claim 1, wherein the film includes a scrolled film.

11. The method of claim 1, wherein the housing is sized and shaped to fit within the ear.

* * * * *

UNITED STATES PATENT AND TRADEMARK OFFICE
CERTIFICATE OF CORRECTION

PATENT NO. : 8,579,794 B2  
APPLICATION NO. : 12/434042  
DATED : November 12, 2013  
INVENTOR(S) : Reinhold Henke Page 1 of 1

It is certified that error appears in the above-identified patent and that said Letters Patent is hereby corrected as shown below:

On the title page, in column 2, Item (56) under "Other Publications", line 1, delete "09739237.7" and insert --09739237.7,--, therefor On the title page, in column 2, Item (56) under "Other Publications", line 1, delete "Respnse" and insert --Response--, therefor On the title page, in column 2, under Item "(57) Abstract", line 5, delete "and" and insert --an--, therefor On title page 3, in column 2, Item (56) under "Other Publications", line 27, delete "Mailed" and insert --mailed--, therefor On title page 3, in column 2, Item (56) under "Other Publications", line 29, delete "12/562,959" and insert --12/562,959,--, therefor On title page 4, in column 1, Item (56) under "Other Publications", line 17, delete "12/557,765 ," and insert --12/557,765,--, therefor Signed and Sealed this  
Second Day of December, 2014

Michelle K. Lee  
*Deputy Director of the United States Patent and Trademark Office*